United States Patent [19]

Chane-Ching

[11] Patent Number: 5,308,548
[45] Date of Patent: May 3, 1994

[54] PREPARING A DISPERSIBLE, SOL-FORMING CERIUM (IV) COMPOSITION

[75] Inventor: Jean-Yves Chane-Ching, Paris, France

[73] Assignee: Rhone-Poulenc Specialities Chimiques, Courbevoie, France

[21] Appl. No.: 910,572

[22] Filed: Jul. 8, 1992

Related U.S. Application Data

[60] Division of Ser. No. 759,870, Sep. 16, 1991, Pat. No. 5,145,605, which is a continuation of Ser. No. 346,293, Apr. 28, 1989, abandoned, which is a continuation of Ser. No. 876,800, Jun. 20, 1986, abandoned.

[30] Foreign Application Priority Data

Jun. 20, 1985 [FR] France ............... 85 09375

[51] Int. Cl.$^5$ ............................................. B01J 13/00
[52] U.S. Cl. .................................... 252/315.4; 534/16
[58] Field of Search ................. 252/313.1, 309, 315.4; 534/16

[56] References Cited

U.S. PATENT DOCUMENTS

| | | | |
|---|---|---|---|
| 2,364,613 | 12/1944 | Ballard et al. | 423/25.1 |
| 3,024,199 | 3/1962 | Pasfield | 252/313.1 |
| 3,087,949 | 4/1963 | Rinse | 534/16 |
| 3,111,375 | 11/1963 | Gottdenker et al. | 23/14.5 |
| 3,112,990 | 12/1963 | Krunmbolz et al. | 23/14.5 |
| 3,148,151 | 9/1964 | Fitch et al. | 252/313.1 |
| 3,359,213 | 12/1967 | Clearfield | 252/313.1 |
| 3,442,817 | 5/1969 | Luebke | 252/313.1 |
| 3,645,910 | 2/1972 | Woodhead | 252/313.1 |
| 3,761,571 | 9/1973 | Woodhead | 423/263 |
| 4,211,667 | 7/1980 | Yamada et al. | 252/313.1 |
| 4,231,893 | 11/1980 | Woodhead | 252/313.1 |
| 4,244,835 | 1/1981 | Block | 252/313.1 |
| 4,545,923 | 10/1985 | Gradett et al. | 252/309 |
| 4,647,401 | 3/1987 | Gradett et al. | 252/309 |
| 4,731,198 | 3/1988 | Watanabe et al. | 252/313.1 |
| 4,886,624 | 12/1989 | Gradett et al. | 252/308 |
| 5,021,192 | 6/1991 | David et al. | 252/313.1 |
| 5,035,834 | 7/1991 | Chane-Ching et al. | 252/313.1 |

Primary Examiner—Edward A. Miller
Attorney, Agent, or Firm—Burns, Doane, Swecker & Mathis

[57] ABSTRACT

Preparing a novel cerium (IV) compound, well adopted for the production of aqueous colloidal sols therefrom, has the general formula (I):

$$Ce(M)_t(CH_3(CH_2)_n COO^-)_x(OH^-)_y(NO_3^-)_z \qquad (I)$$

wherein M is an alkali metal or a quaternary ammonium radical; t ranges from 0.1 to 0.3; n is 0 or 1; x ranges from 0.1 to 0.7; y is a number such that $y = 4 + t - x - z$; and z ranges from 0.3 to 0.6.

20 Claims, No Drawings

PREPARING A DISPERSIBLE, SOL-FORMING CERIUM (IV) COMPOSITION

This application is a divisional of application Ser. No. 07/759,870, filed Sep. 16, 1991, now U.S. Pat. No. 5,145,605, which is a continuation of application Ser. No. 07/346,293 filed Apr. 28, 1989, which is a continuation of application Ser. No. 06/876,800 filed Jun. 20, 1986 (now abandoned).

CROSS-REFERENCE TO RELATED APPLICATIONS

Copending applications Ser. Nos. 06/876,449, 06/876,635 and 06/876,681, all now abandoned, all filed concurrently herewith and all assigned to the assignee hereof.

BACKGROUND OF THE INVENTION

1. Field of the Invention

The present invention relates to a novel compound of cerium (IV) and to a process for the preparation thereof. This invention more especially relates to a novel compound of cerium (IV) that is readily dispersed in water.

2. Description of the Prior Art

It is known to this art, from the Kirk-Othmer *E.cyclopedia of Chemical Technology*, 2nd edition, Vol. 4, p. 850, that a hydrated ceric dioxide of the formula $CeO_2 \cdot xH_2O$ may be prepared, wherein x is a number ranging from 0.5 to 2, in the form of a gelatinous precipitate by the addition of sodium or ammonium to solutions of ceric salts.

It has also been proposed to this art, according to French Patent No. 2,482,075, to prepare a cerium (IV) compound which is dispersible in water by dispersing an essentially dry hydrate of cerium (IV) oxide in an aqueous medium, the same having been subjected to a heat treatment at a temperature ranging from 200° C. to 450° C., in the presence of a disintegrating agent, in particular nitric acid. Heating in the presence of a disintegrating agent effects the disintegration of the aggregated crystallites into hydrated cerium (IV) oxide, thereby producing a dispersible cerium compound.

It is noted in this '075 patent that the preparation of a hydrate of cerium (IV) oxide may be carried out by precipitation beginning with a cerium salt; thus, for example, a high purity cerous carbonate may be dissolved in a nitric acid or hydrochloric acid solution to obtain a neutral solution of cerous nitrate or chloride, which is then oxidized with $NH_4OH/H_2O_2$ to obtain the hydrate of cerium (IV) oxide.

SUMMARY OF THE INVENTION

A major object of the present invention is the provision of a novel compound of cerium (IV) that is easily dispersed in water and which is prepared directly from a cerium (IV) salt without the need for a precipitation stage and separation from ceric hydroxide.

The novel cerium (IV) compound according to this invention has the following general formula (I):

$$Ce(M)_t(CH_3(CH_2)_nCOO^-)_x(OH^-)_y(NO_3^-)_z$$

wherein M is an alkali metal or a quaternary ammonium radical; t ranges from 0.1 to 0.3; n is 0 or 1; z ranges from 0.1 to 0.7; y is a number such that: $y = 4 + t - x - z$; and z ranges from 0.3 to 0.6.

Analysis of this novel compound by X-ray diffraction evidenced that it is a poorly crystallized product having a $CeO_2$ type structure.

The present invention also features a process for the preparation of the novel compound (I) by (i) mixing an aqueous solution of a cerium (IV) salt with acetic acid or propionic acid; (ii) reacting the resulting mixture with a base; (iii) heat treating the mixture of reaction; (iv) separating the precipitate which is thus produced; and thence (v) drying said separated precipitate.

DETAILED DESCRIPTION OF THE PREFERRED EMBODIMENTS OF THE INVENTION

More particularly according to the present invention, in the first stage of the subject process, an aqueous solution of a cerium (IV) salt and acetic or propionic acid, which themselves may be in aqueous solution, is utilized.

The starting solution of the cerium salt according to the invention advantageously is an aqueous solution of ceric nitrate, or an aqueous solution of ceri-ammonium nitrate. The solution may contain, without causing difficulties, cerium in the cerous state, but it is desirable that it contain at least 85% of cerium (IV).

The solution of the cerium salt is selected such that it will not contain impurities which could be transferred into the final product. In particular, it is preferable that it does not contain covalent anions which are coagulating in nature, such as sulfates, and the like. However, small amounts may be tolerated. For example, said anions may constitute up to 5% by weight of the cerium salt, expressed as $CeO_2$.

The concentration of the solution of the cerium salt is not critical according to this invention. If it is expressed in terms of cerium (IV) values, it may advantageously vary from 0.1 to 2 moles per liter. It may be important for the productivity of the equipment employed to use a concentrated solution of the salt of cerium (IV); a concentration of from 1 to 2 moles per liter is preferred.

The aqueous solution of the cerium (IV) salt has a certain initial acidity and may have a normality ranging from 0.1N to 4N. The concentration in $H^+$ ions is not critical. It is desirable that it range from 0.1N to 1N.

The solution of ceric nitrate obtained by the electrolytic oxidation of a solution of cerous nitrate and described in published French Application No. 2,570,087 (No. 84/13641) is one starting material of choice.

The acetic acid or propionic acid is selected such as to be free of impurities. They may be used diluted, for example 1N, or concentrated. Preferably, concentrated commercial acetic or propionic acid is used.

Acetic acid is preferred over propionic acid.

The proportion of acetic acid or propionic acid to be used with respect to that of the cerium (IV) salt is not critical. The molar ratio between the acid and the cerium (IV) salt, expressed as $CeO_2$, advantageously ranges from 0.01 to 15 and preferably from 0.5 to 2.

According to the process of the invention, the mixture is prepared by agitating the aqueous solution of the cerium (IV) salt and the acetic or propionic acid, at a temperature ranging from room temperature to 80° C. It is not advisable to exceed 80° C., in order to prevent the decomposition of the acid.

In the second stage of the process, a base is added to the resulting mixture.

The basic solution used according to the invention may be, in particular, an aqueous solution of ammonium, sodium or potassium hydroxide. Gaseous ammonia may also be used. Consistent herewith, an ammonium solution is the preferred.

The normality of the basic solution is not critical according to the invention; it may vary over a wide range, for example, from 0.1 to 11N, but it is preferable from an economic point of view to use a concentration ranging from 5 to 11N.

The proportion of the basic solution to the solution of the cerium (IV) salt should be such that the molar ratio of OH$^-$/Ce (IV) is greater than or equal to 1 and less than or equal to 4, with OH representing the number of moles of OH$^-$ introduced by the addition of the base and Ce (IV) representing the number of moles of Ce (IV) present in the reaction medium.

Preferably, a molar ratio of OH$^-$/Ce (IV) greater than or equal to 1.5 and less than or equal to 3.5 is selected.

The reaction between the mixture obtained in the first stage and the base added in the amounts defined above, is advantageously carried out at a temperature ranging from 0° C. to 60° C., but preferably at room temperature (most typically 15° to 25° C.).

The duration of the reaction is also not critical and depends upon the capacity of the apparatus employed. It may vary from 1 second to 20 hours.

The mixture of the aforementioned reagents may be carried out according to any one of a number of different embodiments. For example, admixtures of the aqueous solution of the cerium (IV) salt containing the acetic or propionic acid with the basic solution may be carried out simultaneously under agitation, or the base may be added continuously, or in a single batch, to the aqueous solution of the cerium (IV) salt containing the acetic or propionic acid.

In a third stage, the reaction mixture is heat treated at a temperature ranging from 50° C. to 100° C., and preferably from 70° C. to 90° C.

The reaction mixture may be immediately subjected to the selected temperature, or the temperature thereof may be gradually increased to the desired value.

The conditions of the heat treatment are not critical; the treatment may be carried out in air or under an inert atmosphere. Agitation is not necessary during the heat treatment.

The duration of this treatment may vary over a wide range of from 2 to 24 hours, preferably from 4 hours to 24 hours.

Upon completion of this operation, a solid precipitate is recovered, which is then separated by conventional liquid/solid separation methods, i.e., filtration, decantation, centrifugation, and the like.

The product obtained is then dried at a temperature varying from room temperature to 120° C., and preferably from 60° C. to 100° C. This operation may be carried out in air or under a reduced pressure, for example, a pressure of from 1 mm (133.32 Pa) to 100 mm of mercury (13 332.2 Pa). The duration of the drying step is also not critical.

According to the invention, the cerium (IV) compound is prepared in a yield by weight, expressed as $CeO_2$, in relation to the amount of $CeO_2$ introduced via the solution of the cerium (IV) salt, varying from 75 to 98%.

The compound of the invention prepared by the aforedescribed process is capable of directly forming an aqueous dispersion of the cerium (IV) compound, hereinafter referred to as a "sol".

Thus, the present invention also features the aqueous sols formulated from the cerium (IV) compound having the formula (I).

The present invention also provides a process for the preparation of an aqueous sol of a cerium (IV) compound, whereby the compound of cerium (IV) corresponding to the formula (I) is placed in suspension in water.

The nature of the water is not critical and its temperature is generally ambient temperature.

Preferably, the preparation of said sol is carried out under agitation.

In one embodiment of the present invention, the compound of cerium (IV) is present in the form of a colloidal dispersion in water, which signifies that said compound comprises particles of colloidal dimensions, but does not exclude the presence of Ce (IV) in the ionic form.

An aqueous sol of a cerium (IV) compound may be prepared according to the invention in a concentration, expressed as $CeO_2$, of up to 1.5 moles/liter and preferably varying from 0.2 to 1.5 moles/liter.

A sol wherein the dimensions of the colloids vary over a rather wide range may thus be obtained.

The size of the colloids is defined as the measurement of the hydrodynamic diameter of the colloids determined by the quasi-elastic diffusion of light described by Michael L. McConnel in *Analytical Chemistry*, 53, No. 8, 1007 A (1981), with said diameter varying from 100 to 1000 Å.

The sols obtained according to this invention are stable in storage; there is no settling after several months in storage.

In order to further illustrate the present invention and the advantages thereof, the following specific examples are given, it being understood that same are intended only as illustrative and in nowise limitative. In said examples to follow, all parts and percentages are by weight.

EXAMPLE 1

(a) Preparation of a cerium (IV) compound having the formula (I)

Into a three-necked, 2 liter flask, equipped with a thermometer, an agitator, and a system for the introduction of reagents (metering pump), 100 cm$^3$ of a commercial 17.5acetic acid were introduced and mixed at room temperature with 400 cm$^3$ of ceric nitrate solution containing 1.23 molesoliter of cerium (IV), 0.05 mole/liter of cerium (III) and having a free acidity of 0.66N, obtained by electrolysis according to French Application No. 2,570,087.

To this solution, which was maintained under agitation at room temperature for 5 hours, 34 min, a 3.6N ammonium solution was added at a rate of 100 cm$^3$ per hour.

A&ter this addition, the reaction mixture contained cerium (IV) in a concentration, expressed as $CeO_2$, of 80 g/l, in a molar ratio OH$^-$/Ce (IV) of approximately 3.5 and a molar ratio of acetic acid/Ce (IV) of approximately 3.5.

In a second stage, the reaction mixture was subjected to a heat treatment. For this purpose, the reaction mixture obtained above was placed in an oven at 80° C.

After 24 hours, a yellowish white precipitate was recovered by filtration through sintered glass (No. 3 porosity).

The resultant product was then dried in air, in an oven heated to 80° C., for approximately 24 hours.

109.2 g of a precipitate displaying an ignition weight loss of about 25% were recovered.

A yield of the precipitation of cerium equal to 97% was determined.

Chemical analysis of the final product gave the following results (the ratios are molar ratios):
(i) Ce (III)/Ce (IV)=0.02
(ii) $NO_3^-$/Ce (IV)=0.44
(iii) $OH_4^+$/Ce (IV)=0.17
(iv) Acetate/Ce (IV)=0.29

Analysis by X-ray diffraction evidenced the product of the invention to be a poorly crystallized material having a crystalline $CeO_2$ phase of the fluorine type.

(b) Preparation of an aqueous sol of the cerium (IV) compound of the invention 45.86 g of the compound prepared in step (a) were added to distilled water in an amount sufficient to provide a total volume of 200 cm³.

A sol having a clear appearance and a concentration in cerium (IV), expressed as $CeO_2$, of 172 g/l (1 mole/liter) was prepared.

Examination by quasi-elastic light diffusion evidenced the presence of colloids having a hydrodynamic diameter on the order of 300 Å.

It is noted that the sol obtained was stable in storage and exhibited no settling after at least one year.

EXAMPLE 2

(a) The procedure of Example 1 was repeated, with the following differences
(i) 400 cm³ of a solution of ceric nitrate containing 1.23 moles/liter of cerium (IV), 0.05 mole/liter of cerium (III) and having a free acidity of 0.66N, were used;
(ii) 400 cm³ of concentrated 17.5N acetic acid, were used; and
(iii) 138 cm³ of an 11ammonium solution were used, comprising 118 cm³ of added water.

Upon completion of the reaction, the reaction mixture contained cerium (IV) in a concentration, expressed as $CeO_2$ equal to 80 g/l, a molar ratio $OH^-$/Ce (IV) of approximately 2.5 and a molar acetic acid/Ce (IV) ratio of about 14.

In a second stage, the reaction mixture was subjected to a heat treatment in an oven at 100° C. for 24 hours.

After drying in air, 68.30 g of a product having the following chemical analysis were recovered:
$CeO_2$=70%
Molar ratio, acetate/Ce (IV)=0.67

(b) A sol as in Example 1 was prepared by the addition of 49.14 g of the product obtained above to distilled water in an amount sufficient to provide a volume of 200 cm³.

A sol having a cerium (IV) concentration, expressed as $CeO_2$, of 172 g/l, was obtained.

Examination by quasi-elastic light diffusion carried out on an aliquot fraction diluted to 0.35 mole/liter of cerium (IV) showed the presence of colloids having a hydrodynamic diameter of approximately 150 Å.

EXAMPLE 3

(a) The procedure of Example 1 was again repeated, with the following differences (i) 450 cm³ of a ceric nitrate solution were used, containing 1.23 moles/liter of cerium (IV), 0.05 mole/liter cerium (III) and having a free acidity of 0.66;
(ii) 50 cm³ of concentrated commercial acetic acid of approximately 17.5were used; and
(iii) 693 cm³ of a 3.14N ammonium solution were used.

Upon completion of the reaction, the reaction mixture contained cerium (IV) in a concentration, expressed as $CeO_2$, equal to 80 g/l, a molar ratio $OH^-$/Ce (IV) of approximately 3.5 and a molar ratio, acetic acid/Ce (IV), of about 1.55.

In a second stage, the reaction mixture was subjected to a heat treatment in an oven at 100° C. for 24 hours.

After drying in air, 122 g of a product containing 70.5% $CeO_2$ were obtained.

(b) A sol was prepared as in Example 1 by the addition of 48.79 g of the product obtained above to distilled water, in an amount sufficient to provide a total volume of 200 cm³.

A sol having a cerium (IV) concentration, expressed as $CeO_2$, of 172 g/l, was obtained.

Examination by quasi-elastic light diffusion carried out on an aliquot fraction showed the presence of colloids having a hydrodynamic diameter of approximately 200 Å.

EXAMPLE 4

(a) The procedure of Example 1 was again repeated, but with the following differences
(i) 500 cm³ of a ceric nitrate solution were used, containing 1.54 moles/liter of cerium (IV), 0.08 mole/liter cerium (III) and having a free acidity of 0.415;
(ii) 44 cm³ concentrated 17.5N acetic acid were used; and
(iii) 1111.5 cm³ of a 2.61ammonium solution were used.

The reaction mixture contained cerium (IV) in a concentration, expressed as $CeO_2$, of 80 g/l, a molar ratio $OH^-$/Ce (IV) of approximately 3.5 and a molar ratio acetic acid/Ce (IV) equal to 1.

In a second stage, the reaction mixture was subjected to a heat treatment. For this purpose, the reaction mixture obtained above was placed in an oven heated to a temperature of 100° C.

A&ter 12 hours, a precipitate was recovered by filtration on sintered glass (No. 4 porosity).

The product obtained was then subjected to drying in air, carried out in an oven at 80° C. for approximately 24 hours.

161.3 g of a product having the following chemical analysis were recovered:
(i) $CeO_2$=75%
(ii) Molar ratio $NO_3^-$/Ce (IV)=0.53
(iii) Molar ratio $OH_4^+$/Ce (IV)=0.26
(iv) Molar ratio acetic acid/Ce (IV)=0.2

A cerium precipitation yield of 95% was determined.

X-ray diffraction analysis showed that the product obtained was poorly crystallized and had a crystalline $CeO_2$ phase: the proportion of crystallization determined with respect to a control sample was approximately 35% and the size of the elementary crystallites was less than 30 Å.

(b) 45.86 g of the compound prepared according to step (a) were added to distilled water in an amount sufficient to provide a volume of 200 cm³.

A sol having a clear appearance and a cerium (IV) concentration, expressed as CeO$_2$, of 172 g/l (1 mole/liter), was obtained.

Examination by quasi-elastic light diffusion showed the presence of colloids having a hydrodynamic diameter on the order of 140 Å.

It was noted that the sol obtained had good stability in storage and evidenced no settling over time.

EXAMPLE 5

The procedure of Example 1 was again repeated, but with the following differences:

(i) 500 cm$^3$ of a ceric nitrate solution were used, containing 1.54 moles/liter of cerium (IV), 0.08 mole/liter cerium (III) and having a free acidity of 0.415N;

(ii) 57 cm$^3$ concentrated, 99% commercial propionic acid (d=0.99 to 1.00) were used; and (iii) 1098 cm$^3$ of a 1.59N ammonium solution were used.

Upon completion of the reaction, the mixture contained cerium (IV) in a concentration, expressed as CeO$_2$, equal to 80 g/l, a molar ratio OH$^-$/Ce (IV) of approximately 2 and a molar ratio propionic acid/Ce (IV) of 1.

In a second stage, the reaction mixture was subjected to a heat treatment in an oven at 80° C. for 24 hours.

After drying in air, 84.1 g of a product containing 75% CeO$_2$ were recovered.

A precipitation yield in cerium equal to 47.6% was determined.

(b) A sol was prepared as in Example 1, by the addition of 45.86 g of the product obtained above to distilled water in an amount sufficient to provide a volume of 200 cm$^3$.

A sol was obtained having a concentration in cerium (IV), expressed in CeO$_2$, of 172 g/l (1 mole/liter).

Examination by quasi-elastic light diffusion carried out on an aliquot fraction showed the presence of colloids having a hydrodynamic diameter of approximately 345 Å.

It was noted that the sol obtained had good stability in storage and did not exhibit settling over time.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of 4he following claims, including equivalents thereof.

What is claimed is:

1. A process for the preparation of a cerium (IV) material selected from the group of materials having the general formula (I):

$$Ce(M)_t(CH_3[CH_2]_nCOO^-)_x(OH^-)_y(NO_3^-)_z \qquad (I)$$

wherein M is an alkali metal or a quaternary ammonium radical; t ranges from 0.1 to 0.3; n is 0 or 1; x ranges from 0.1 to 0.7; y is a number such that y=4+t−x−z; and z ranges from 0.3 to 0.6, comprising (i) forming an admixture by admixing an aqueous solution of a cerium (IV) nitrate salt with acetic or propionic acid, (ii) forming a reaction medium by reacting the admixture with a base, (iii) heating the reaction medium and producing a precipitate of said cerium (IV) material, (iv) separating the precipitate, and (v) drying said precipitate.

2. The process as defined by claim 1, wherein in step (i) the aqueous solution of the salt of cerium (IV) comprises an aqueous solution of ceric nitrate or an aqueous solution of ceri-ammonium nitrate.

3. The process as defined by claim 1, wherein the cerium (IV) salt in step (i) has a concentration, expressed as cerium (IV), ranging from 0.1 to 2 moles/liter.

4. The process as defined by claim 3, wherein said concentration of the salt of cerium (IV), expressed as cerium (IV), ranges from 1 to 2 moles/liter.

5. The process as defined by claim 1, wherein in step (i) a molar ratio of 4he acetic or propionic acid to the salt of cerium (IV), expressed as CeO$_2$, ranges from 0.01 to 15.

6. The process as defined by claim 5, wherein the molar ratio of the acetic or propionic acid to the salt of cerium (IV), expressed as CeO$_2$, ranges from 0.5 to 2.

7. The process as defined by claim 1, wherein the step (i) of admixing the aqueous solution of the salt of cerium (IV) with the acetic or propionic acid is carried out at a temperature of from ambient to 80° C.

8. The process as defined by claim 1, wherein the base reacted in step (ii) comprises an aqueous solution of ammonia, sodium or potassium hydroxide, or gaseous ammonia.

9. The process as defined by claim 8, wherein the normality of the solution of base reacted in step (ii) ranges from 0.1 to 11.

10. The process as defined by claim 9, wherein the normality of the solution of base reacted in step (ii) ranges from 5 to 11N.

11. The process as defined by claim 8, wherein in step (ii) a molar ratio OH$^-$/Ce (IV) in the reaction medium is greater than or equal to 1 and less than or equal to 4.

12. The process as defined by claim 11, wherein said molar ratio OH$^-$/Ce (IV) is greater than or equal to 1.5 and less than or equal to 3.5.

13. The process as defined by claim 1, wherein the reaction in step (ii) between the admixture and the base is carried out at a temperature ranging from 0° C. to 60° C.

14. The process as defined by claim 13, wherein said reaction in step (ii) is carried out at ambient temperature.

15. The process as defined by claim 8, wherein in step (ii) the base is in a base solution and the admixture and the base solution are simultaneously mixed together under agitation, or the base is added continuously or batchwise to the admixture.

16. The process as defined by claim 1, wherein in step (iii) the reaction medium is heated to a temperature ranging from 50° C. to 100° C.

17. The process as defined by claim 16, wherein said heating in step (iii) is to a temperature ranging from 70° C. to 90° C.

18. The process as defined by claim 16, wherein the duration of said heating in step (iii) ranges from 2 to 24 hours.

19. The process as defined by claim 18, wherein the duration of said heating in step (iii) ranges from 4 to 24 hours.

20. The process as defined by claim 1, wherein in step (v) said precipitate is dried at a temperature ranging from ambient temperature to 120° C.